United States Patent
Levy et al.

(10) Patent No.: US 9,540,412 B2
(45) Date of Patent: Jan. 10, 2017

(54) METHODS OF PREPARING TARGETED APTAMER PRODRUGS

(75) Inventors: Matthew Levy, New Rochelle, NY (US); Amy Yan, New Rochelle, NY (US); Brian Wengerter, Bronx, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 8 days.

(21) Appl. No.: 13/643,408

(22) PCT Filed: Apr. 29, 2011

(86) PCT No.: PCT/US2011/000754
§ 371 (c)(1),
(2), (4) Date: Jan. 15, 2013

(87) PCT Pub. No.: WO2011/142798
PCT Pub. Date: Nov. 17, 2011

(65) Prior Publication Data
US 2013/0123478 A1    May 16, 2013

Related U.S. Application Data

(60) Provisional application No. 61/395,468, filed on May 13, 2010.

(51) Int. Cl.
| | | |
|---|---|---|
| *A61K 48/00* | (2006.01) | |
| *C07H 21/04* | (2006.01) | |
| *C12N 15/11* | (2006.01) | |
| *C12N 15/115* | (2010.01) | |
| *C12N 15/87* | (2006.01) | |
| *C07H 21/02* | (2006.01) | |
| *C12Q 1/68* | (2006.01) | |

(52) U.S. Cl.
CPC ............. *C07H 21/04* (2013.01); *C12N 15/111* (2013.01); *C12N 15/115* (2013.01); *C12N 15/87* (2013.01); *A61K 48/00* (2013.01); *C12N 2310/11* (2013.01); *C12N 2310/16* (2013.01); *C12N 2310/334* (2013.01); *C12N 2310/335* (2013.01); *C12N 2310/3519* (2013.01); *C12N 2320/13* (2013.01); *C12N 2320/32* (2013.01)

(58) Field of Classification Search
CPC ................................................. C12N 15/113
See application file for complete search history.

(56) References Cited

U.S. PATENT DOCUMENTS

| | | | | |
|---|---|---|---|---|
| 6,562,798 | B1 * | 5/2003 | Schwartz ................. | 514/44 R |
| 6,610,841 | B1 * | 8/2003 | Warren ............ | A61K 47/48092 |
| | | | | 435/6.16 |
| 2006/0105975 | A1 * | 5/2006 | Pendergrast et al. ........... | 514/44 |
| 2009/0081679 | A1 * | 3/2009 | Keefe et al. ..................... | 435/6 |
| 2009/0105172 | A1 | 4/2009 | Diener | |
| 2009/0148944 | A1 * | 6/2009 | Rossi et al. .................. | 435/375 |
| 2009/0170711 | A1 * | 7/2009 | Ellington et al. ................. | 506/1 |

OTHER PUBLICATIONS

Dollins et al., Assembling OX40 aptamers on a molecular scaffold to create a receptor-activating aptamer, 2008, Chemistry & Biology, vol. 15, pp. 675-682.*
Javier et al., Aptamer-targeted gold nanoparticles as molecular-specific contrast agents for reflectance imaging, 2008, Bioconjugate Chemistry, vol. 19, pp. 1309-1312.*
Lupold et al., Identification and characterization of nuclease-stabilized RNA molecules that bind human prostate cancer cells via the prostate-specific membrane antigen, 2002, Cancer Research, vol. 62, pp. 4029-4033.*
Yan, Amy C., et al. "Aptamers and Aptamer Targeted Delivery." RNA Biology 2009; 6(3): 316-320; p. 218.
International Search Report and Written Opinion dated Apr. 29, 2011 corresponding to International Application No. PCT/US11/00754.

* cited by examiner

*Primary Examiner* — Dana Shin
(74) *Attorney, Agent, or Firm* — Amster, Rothstein & Ebenstein LLP

(57) ABSTRACT

The present invention provides methods of preparing an oligonucleotide, nucleoside or nucleoside analog for selective introduction into a subject's cells, the method comprising (1) selecting a targeted aptamer, internalizing nucleic acid or tumor-homing nucleic acid via iterative rounds of selection, and (i) hybridizing it to an oligonucleotide, (ii) replacing one or more nucleotide with a nucleoside or nucleoside analog, or (iii) synthesizing the it with one or more nucleoside or nucleoside analogs; or (2) preparing a naive combinatorial aptamer, internalizing nucleic acid or tumor-homing nucleic acid prodrug library, and running iterative rounds of selection for the cells. The present invention also provides the agent, the pharmaceutical composition, and methods of treating or preventing cancer and/or viral infection, the method comprising administration of the oligonucleotide, nucleoside or nucleoside analog for selective introduction into a subject's cells.

4 Claims, 6 Drawing Sheets

METHODS OF PREPARING TARGETED APTAMER PRODRUGS

CROSS-REFERENCE TO RELATED APPLICATIONS

This application is a U.S. national stage entry under 35 U.S.C. §371 of PCT International Patent Application No. PCT/US2011/000754, filed Apr. 29, 2011, which claims benefit of U.S. Provisional Application No. 61/395,468, filed May 13, 2010, the contents of each of which are hereby incorporated by reference.

FIELD OF THE INVENTION

The present invention relates generally to methods of preparing targeted aptamer, internalizing nucleic acid or tumor-homing nucleic acid prodrugs as well as the targeted aptamer, internalizing nucleic acid or tumor-homing nucleic acid prodrugs themselves.

BACKGROUND OF THE INVENTION

Throughout this application various publications are referred to in parenthesis. Full citations for these references may be found at the end of the specification. The disclosures of these publications are hereby incorporated by reference in their entirety into the subject application to more fully describe the art to which the subject invention pertains.

From laboratory to clinic, directing therapeutics to specific sites (cells, tumors, tissues) and ensuring that the delivered agents will be active only at the desired sites remains a daunting challenge. Targeting is a particularly critical issue in cancer therapy because of the undesirable side effects of chemotherapeutic agents, many of which can also be toxic to normal cells.

Other technologies have attempted to engineer drug-delivery vehicles that act solely on targeted cells. For example, antibodies have emerged as important players in developing next generation cancer drugs, where they are being used not only as inhibitors, but also for targeted delivery of drugs, toxins and other molecules (reviewed in Carter and Senter 2008; Wu and Senter 2005). The strategy for using antibodies as targeting agents typically involves chemically conjugating the drug of choice to an antibody that recognizes a cell surface receptor. Most commonly, the targeted receptor is known to undergo receptor-mediated endocytosis, which leads to internalization of the targeted cargoes followed by release of the chemotherapeutic agent. While, this approach should be simple and effective, the use of antibodies as therapeutics is somewhat hampered by the need to engineer 'humanized' variants of these proteins that would not be immunogenic. Moreover, while numerous antibody drug conjugation strategies exist, almost all rely on conjugation through surface exposed amino groups (lysines), sulfhydryls (cysteines), or sugars (sialic acids) in these large (150 kDa) proteins. Precise control of drug placement, therefore, is nearly impossible and can compromise antibody function. The resultant conjugates are typically heterogeneous in nature, which can affect consistency in both production as well as efficacy.

The potential problems associated with using antibodies for targeted delivery of drugs has led to investigations into a variety of alternative targeting agents including antibody fragments such as Fabs, diabodies or single chain antibody fragments (Wu and Senter 2005). These engineered portions of antibodies do offer some advantages over full antibodies. In particular, their smaller size (25-40 kDa) aids in extravasation and tissue penetration. Additionally, they can be further engineered to facilitate some conjugation strategies; however, issues with immunity are still a factor. Small peptides, too, can be used for targeting cargoes. These small molecules, typically 8-10 amino acids in length, have generally been isolated using a method called phage display (McGuire et al. 2009); however, such reagents often require multivalent presentation for efficient targeting which can complicate their synthesis and production (Oyama et al. 2003).

The present invention provides an attractive alternative involving a novel system for the targeted delivery of drugs that specifically target tumor cells in whole animals. To do this, an alternate class of targeting molecules composed of nucleic acids called aptamer, internalizing nucleic acid or tumor-homing nucleic acids are used. The present invention also provides the molecules so-identified. These delivery aptamers, internalizing nucleic acids or tumor-homing nucleic acids are composed of cytotoxic nucleoside analogs and are engineered to target specific cells.

SUMMARY OF THE INVENTION

The present invention provides a method of preparing an oligonucleotide for selective introduction into a subject's cells, the method comprising selecting a targeted aptamer, internalizing nucleic acid or tumor-homing nucleic acid via iterative rounds of selection, and (i) hybridizing an oligonucleotide to the targeted aptamer, internalizing nucleic acid or tumor-homing nucleic acid; (ii) replacing one or more nucleotide with a nucleoside or nucleoside analog; or (iii) synthesizing the targeted aptamer, internalizing nucleic acid or tumor-homing nucleic acid with one or more nucleoside or nucleoside analog.

The present invention also provides a method of preparing a nucleoside or nucleoside analog for selective introduction into a subject's cells, the method comprising preparing a naïve combinatorial aptamer, internalizing nucleic acid or tumor-homing nucleic acid prodrug library, and running iterative rounds of selection for the cells.

The present invention provides the oligonucleotide, nucleoside or nucleoside analog prepared for selective introduction in a subject's cells by (1) selecting a targeted aptamer, internalizing nucleic acid or tumor-homing nucleic acid via iterative rounds of selection, and hybridizing an oligonucleotide to the targeted aptamer, internalizing nucleic acid or tumor-homing nucleic acid; (2) selecting a targeted aptamer, internalizing nucleic acid or tumor-homing nucleic acid via iterative rounds of selection, and replacing one or more nucleotide with a nucleoside or nucleoside analog; (3) selecting a targeted aptamer, internalizing nucleic acid or tumor-homing nucleic acid via iterative rounds of selection, and synthesizing the targeted aptamer, internalizing nucleic acid or tumor-homing nucleic acid with one or more nucleoside or nucleoside aptamer, internalizing nucleic acid or tumor-homing nucleic acids; or (4) preparing a naïve combinatorial aptamer, internalizing nucleic acid or tumor-homing nucleic acid prodrug library, and running iterative rounds of selection for the cells.

The present invention additionally provides an oligonucleotide, nucleoside or nucleoside analog prepared for selective introduction into a subject's cells of SEQ ID NOS:9 or 10 or SEQ ID NO:6 hybridized to SEQ ID NO:7.

The present invention provides a targeted aptamer, internalizing nucleic acid or tumor-homing nucleic acid selected by the method of any of (1) selecting a targeted aptamer, internalizing nucleic acid or tumor-homing nucleic acid via iterative rounds of selection, and hybridizing an oligonucleotide to the targeted aptamer, internalizing nucleic acid or tumor-homing nucleic acid; (2) selecting a targeted aptamer, internalizing nucleic acid or tumor-homing nucleic acid via iterative rounds of selection, and replacing one or more nucleotide with a nucleoside or nucleoside analog; (3) selecting a targeted aptamer, internalizing nucleic acid or tumor-homing nucleic acid via iterative rounds of selection, and synthesizing the targeted aptamer, internalizing nucleic acid or tumor-homing nucleic acid with one or more nucleoside or nucleoside aptamer, internalizing nucleic acid or tumor-homing nucleic acids; or (4) preparing a naïve combinatorial aptamer, internalizing nucleic acid or tumor-homing nucleic acid prodrug library, and running iterative rounds of selection for the cells, wherein the targeted aptamer, internalizing nucleic acid or tumor-homing nucleic acid comprises the targeted aptamer, internalizing nucleic acid or tumor-homing nucleic acid of SEQ ID NOS: 1, 2, 3, 4, 5, 6, 11 or 12.

The present invention further provides a targeted aptamer, internalizing nucleic acid or tumor-homing nucleic acid of SEQ ID NOS: 1, 2, 3, 4, 5, 6, 11 or 12.

The present invention additionally provides a pharmaceutical composition comprising a therapeutically effective amount of the oligonucleotide, nucleoside or nucleoside analog prepared for selective introduction in a subject's cells in a pharmaceutically acceptable carrier.

The present invention further provides a method of protecting or treating a subject from cancer or viral infection, the method comprising administering to the subject a therapeutically effective amount of an oligonucleotide, nucleoside or nucleoside analog prepared for selective introduction in a subject's cells or a pharmaceutical composition thereof.

The present invention additionally provides the use of an oligonucleotide, nucleoside or nucleoside analog prepared for selective introduction in a subject's cells to protect or treat the subject from cancer or viral infection. For example, the oligonucleotide, nucleoside or nucleoside analog prepared for selective introduction in a subject's cells may be the oligonucleotide, nucleoside or nucleoside analog of SEQ ID NO:9, SEQ ID NO:10, or SEQ ID NO:6 hybridized to SEQ ID NO:7.

DETAILED DESCRIPTION OF THE INVENTION

Figure 1:
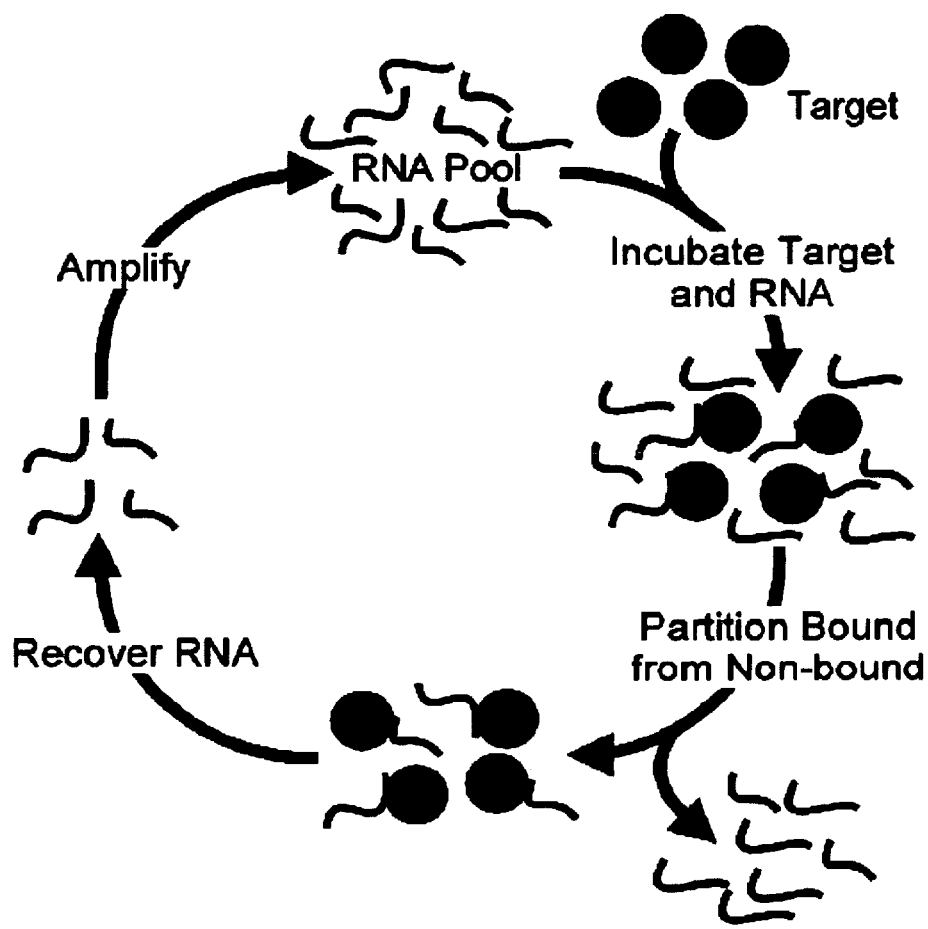
FIG. 1. In vitro iterative selection of aptamer, internalizing nucleic acid or tumor-homing nucleic acids.

The present invention provides a method of preparing an oligonucleotide for selective introduction into a subject's cells, the method comprising selecting a targeted aptamer, internalizing nucleic acid or tumor-homing nucleic acid via iterative rounds of selection, and (i) hybridizing an oligonucleotide to the targeted aptamer, internalizing nucleic acid or tumor-homing nucleic acid; (ii) replacing one or more nucleotide with a nucleoside or nucleoside analog; or (iii) synthesizing the targeted aptamer, internalizing nucleic acid or tumor-homing nucleic acid with one or more nucleoside or nucleoside analog.

The present invention also provides a method of preparing a nucleoside or nucleoside analog for selective introduction into a subject's cells, the method comprising preparing a naïve combinatorial aptamer, internalizing nucleic acid or tumor-homing nucleic acid prodrug library, and running iterative rounds of selection for the cells.

Aptamers are RNA or DNA molecules, or comprise both ribonucleotide residues and deoxyribonucleotide residues, and are generally generated from large combinatorial libraries ($10^{14}$-$10^{15}$) of nucleic acids. This may be done by any method known in the art, such as by a process of in vitro selection or by SELEX (Systematic Evolution of Ligands by Exponential Enrichment) which target a specific protein or molecular target. They are generated though a process that relies on binding. Aptamers are thus nucleic acids (oligonucleotides) which bind a specific protein or molecular target, typically with nanomolar or subnanomolar affinity. Generally, aptamers discriminate against molecules closely related to the target molecule.

Internalizing nucleic acids is a class of molecule which is characterized by the direct identification of nucleic acids from large combinatorial libraries ($10^{14}$-$10^{15}$) which are internalized by cells. They can be generated by a process that relies on the selection for function, the ability to internalize into cells. The details of such process are described in U.S. patent application Ser. No. 12/100,390, Publication No. 2009/0170711, entitled "Selection Method for Cell Internalizing Nucleic Acids," herein incorporated in its entirety by reference. To find targeted binding and/or internalizing nucleic acids, iterative rounds of selection are performed. This involves a first round involving introducing a naïve library of nucleic acids and determining which bind and/or are internalized. In successive rounds, only those which bound and/or were internalized in the previous round are used. In this manner, only those internalizing nucleic acids which most strongly or most specifically bind and/or are integrated are selected.

Tumor-homing nucleic acids is a class of molecules which has only recently been reported in the literature and are characterized by the direct identification of nucleic acids from large combinatorial libraries ($10^{14}$-$10^{15}$) that home to tumors in live animals. The results have only recently been published in the journal Nature Chemical Biology (Mi et al., Nat Chem. Biol. 2010 January; 6(1):22-4).

An oligonucleotide attached to a targeted aptamer, internalizing nucleic acid or tumor-homing nucleic acid, or a targeted aptamer, internalizing nucleic acid or tumor-homing nucleic acid with one or more nucleotide replaced with a nucleoside or nucleoside aptamer, internalizing nucleic acid or tumor-homing nucleic acid will be selectively introduced to the cell targeted by the aptamer, internalizing nucleic acid or tumor-homing nucleic acid for binding and/or internalization. Once the aptamer, internalizing nucleic acid or tumor-homing nucleic acid is targeted to a particular cell or cell type, the aptamer, internalizing nucleic acid or tumor-homing nucleic acid will preferentially carry the oligonucleotide, nucleoside or nucleoside analog to that cell or cell type, as opposed to any other cell or cell type. Since the aptamer, internalizing nucleic acid or tumor-homing nucleic acid will bind and/or be internalized by the particular cell or cell line, the oligonucleotide, nucleoside or nucleoside analog will effectively be selectively introduced to that particular cell or cell line.

A "nucleoside" as used herein is a glycosylamine consisting of a base bound to a ribose or deoxyribose sugar via a beta-glycosidic linkage. Examples include cytidine, uridine, adenosine, guanosine, thymidine and inosine. Nucleosides can be phosphorylated by specific kinases in the cell on the sugar's primary alcohol group ($-CH_2-OH$), producing nucleotides, which are the molecular building blocks of DNA and RNA. Nucleosides can be produced by de novo synthesis pathways, particularly in the liver, but they are more abundantly supplied via ingestion and digestion of nucleic acids in the diet, whereby nucleotidases break down nucleotides (such as the thymine nucleotide) into nucleosides (such as thymidine) and phosphate.

A "nucleoside analog" is a nucleoside structurally similar to the naturally occurring residues in RNA and DNA, used in medicine and in molecular biology, and which can be incorporated, e.g. chemically, into an oligonucleotide or nucleic acid by formation of a phosphodiester bond or equivalent with one or two residues of the residue chain depending on whether the nucleoside analog is in a terminal or intra-chain position, respectively. Nucleic acids are chains of nucleotides, which are composed of three parts: a phosphate backbone, a pucker-shaped pentose sugar, either ribose or deoxyribose, and one of five nucleobases. A nucleoside analogue differs from a nucleoside by having any one or more of its hydroxyl, base or sugar groups altered, as long as the alteration does not prevent the nucleoside analogue from being incorporated into an oligonucleotide such as an aptamer, internalizing nucleic acid or tumor-homing nucleic acid. In an embodiment of the invention the nucleoside analogue(s) are one or more of the following: a deoxyadenosine analog, a deoxycytidine analog, a deoxyguanosine analog, a (deoxy-)thymidine analog, and/or a deoxyuridine analog. Typically the analogue nucleobases confer, among other things, different base pairing and base stacking proprieties. Several nucleoside analogues are used as antiviral or anticancer agents. In the cells, these antiviral or anticancer agents are activated by being converted into nucleotides, however they are administered as nucleosides since charged nucleotides cannot easily cross cell membranes.

Nucleoside analogs as envisaged in the current invention include, but are not limited to, cytosine arabinoside, fludarabine, cladribine, acyclovir, 2',3'-dideoxyinosine; 9-β-D-ribofuranosyladenine; 1β-arabinofuranosylcytosine; arabinosylcytosine; 4-amino-5-fluoro-1-[(2R,5S)-2-(hydroxymethyl)-1,3-oxathiolan-5-yl]-1,2-dihydropyrimidin-2-one; 2',3'-dideoxy-3'-thiacytidine; 2'-3'-dideoxycytidine; {(1S,4R)-4-[2-amino-6-(cyclopropylamino)-9H-purin-9-yl]cyclopent-2-en-1-yl}methanol; 2-Amino-9-[(1S,3R,4S)-4-hydroxy-3-(hydroxymethyl)-2-methylidenecyclopentyl]-6,9-dihydro-3H-purin-6-one; 2'-3'-didehydro-2'-3'-dideoxythymidine; 1-(2-deoxy-(3-L-erythro-pentofuranosyl)-5-methylpyrimidine-2,4(1H,3H)-dione; 1-[(2R,4S,5S)-4-azido-5-(hydroxymethyl)oxolan-2-yl]-5-methylpyrimidine-2,4-dione; 1-[(2R,4S,5R)-4-hydroxy-5-(hydroxymethyl)oxolan-2-yl]-5-iodo-1,2,3,4-tetrahydropyrimidine-2,4-dione; 1-[4-hydroxy-5-(hydroxymethyl)oxolan-2-yl]-5-(trifluoromethyl)pyrimidine-2,4-dione; 5-Fluoro-2'-deoxycytidine; 5-Fluorodeoxycytidine; Floxuridine (5-Fluoro-1-[4-hydroxy-5-(hydroxymethyl)tetrahydrofuran-2-yl]-1H-pyrimidine-2,4-dione); 4-amino-1-(2-deoxy-2,2-difluoro-β-D-erythro-pentofuranosyl)pyrimidin-2(1H)-one; 2',2'-difluoro-2'-deoxycytidine; (8R)-3-(2-deoxy-β-D-erythro-pentofuranosyl)-3,4,7,8-tetrahydroimidazo[4,5-d][1,3]diazepin-8-ol.

Aptamers, internalizing nucleic acids and/or tumor-homing nucleic acids of the present invention can be administered by subcutaneous injection (aptamer bioavailability via subcutaneous administration is >80% in monkey studies (Tucker et al., J. Chromatography B. 732: 203-212, 1999)). With good solubility (>150 mg/mL) and comparatively low molecular weight (aptamer: 10-50 kDa; antibody: 150 kDa), a weekly dose of aptamer may be delivered by injection in a volume of less than 0.5 mL. In addition, the small size of aptamers allows them to penetrate into areas of conformational constrictions that do not allow for antibodies or antibody fragments to penetrate, presenting yet another advantage of aptamer-based therapeutics or prophylaxis.

Once functional sequences of aptamers, internalizing nucleic acids and/or tumor-homing nucleic acids are identified, including inclusion of the one or more nucleoside analogs, the molecules can be chemically synthesized if desired, or transcribed from appropriate encoding nucleic acids. The aptamers, internalizing nucleic acids and/or tumor-homing nucleic acids of the present invention, with or without included one or more nucleoside analogs, can be stored in a variety of forms, including as lyophilized powders.

The present invention provides aptamers, internalizing nucleic acids and/or tumor-homing nucleic acids that are ribonucleic acid or deoxyribonucleic acid or mixed ribonucleic acid and deoxyribonucleic acid. Aptamers, internalizing nucleic acids and/or tumor-homing nucleic acids of the invention may be single stranded ribonucleic acid or deoxyribonucleic acid or mixed ribonucleic acid and deoxyribonucleic acid. In some embodiments, the aptamers, internalizing nucleic acids and/or tumor-homing nucleic acids of the invention comprises at least one chemical modification (other than the included nucleoside analog(s), if included). In some embodiments, the chemical modification is selected from the group consisting of: a chemical substitution at a sugar position; a chemical substitution at a phosphate position; and a chemical substitution at a base position, of the nucleic acid. In other embodiments, the chemical modification is selected from the group consisting of: incorporation of a modified nucleotide, 3' capping, conjugation to a high molecular weight, non-immunogenic compound, conjugation to a lipophilic compound, and incorporation of phosphorothioate into the phosphate back bone. In a preferred embodiment, the non-immunogenic, high molecular weight compound is polyalkylene glycol, more preferably polyethylene glycol. In an embodiment the chemical modification is an inverted thymidine cap. In an embodiment the chemical modification is once or more phosphorothioate backbone modification(s).

In order to treat or prevent viral infection or cancers, antiviral and/or anticancer agents can be administered to a subject. However, the agents may negatively affect cells other than those virally infected cells or cancer cells, resulting in side effects, some of which may be severe enough to preclude the use of the agent in vivo. Administering the agent to only the affected cells, or targeting the agent to preferentially localize or internalize to the affected cells may reduce the frequency of, or mitigate the severity of, side effects. Thus, the specific delivery afforded by attaching the drug to or making the drug part of an aptamer, internalizing nucleic acid or tumor-homing nucleic acid is very useful.

As used herein, "selective introduction," or grammatical equivalent thereof, means introduction of the entity being "selectively introduced" into the target in preference to other targets. For example, an oligonucleotide for selectively introduced into a cardiac cell is accumulated into the cardiac cell in preference to a kidney cell or stem cell.

As used herein, "cells corresponding to," referenced cells or grammatical equivalent thereof means cells of the same type. For example, cells corresponding to a subject's cells wherein, for example, the subject's cells being referenced are cardiomyocytes and the subject is a human, are human cardiomyocyte cells.

As used herein "and/or", for example as in option A and/or option B, means the following embodiments: option A, option B, and the option A plus B.

An oligonucleotide is a short nucleic acid polymer, typically with twenty or fewer bases. However, oligonucleotides of up to 200 bases can be synthesized. In the present invention, the oligonucleotide is preferably between 2 and 30 nucleoside or nucleoside analog bases long. Most preferably, the oligonucleotide is between 5 and 25 nucleoside or nucleoside analog bases long. The oligonucleotide can be hybridized, or attached to an aptamer, internalizing nucleic acid or tumor-homing nucleic acid via a non-covalent sequence-specific interaction, to a targeted aptamer, internalizing nucleic acid or tumor-homing nucleic acid by any means known in the art.

The oligonucleotide, nucleoside or nucleoside analog may be any chemotherapeutic known in the art. Preferably, the oligonucleotide, nucleoside or nucleoside analog is an anticancer or antiviral nucleoside analog.

A nucleoside or nucleoside analog for selective introduction into a subject's cells may be created by various methods such as (1) transcription, (2) synthesis, (3) direct selection.

In the transcription method, a targeted aptamer, internalizing nucleic acid or tumor-homing nucleic acid is first determined and then one or more of the nucleotide residues is replaced with a nucleoside or nucleoside analog. This replacement comprises transcribing the targeted aptamer, internalizing nucleic acid or tumor-homing nucleic acid and incorporating the nucleoside or nucleoside analog during transcription. Transcription comprises creating an equivalent copy of the aptamer, internalizing nucleic acid or tumor-homing nucleic acid. In one method, the aptamer, internalizing nucleic acid or tumor-homing nucleic acid is a DNA aptamer, internalizing nucleic acid or tumor-homing nucleic acid and RNA polymerase is used to transcribe the DNA aptamer, internalizing nucleic acid or tumor-homing nucleic acid and create and equivalent RNA aptamer, internalizing nucleic acid or tumor-homing nucleic acid. During the transcription process, nucleosides or nucleoside analogs can be incorporated into the newly created aptamer, internalizing nucleic acid or tumor-homing nucleic acid instead of one or more nucleotide. The nucleoside or nucleoside analog can be incorporated by any method known in the art, for example, transcribing in the presence of the free nucleoside or nucleoside analog. This incorporation can be done by any method known in the art. Preferably, the incorporation of the nucleoside or nucleoside analog does not compromise the binding ability or specificity of the targeted aptamer, internalizing nucleic acid or tumor-homing nucleic acid.

In the synthesis method, a targeted aptamer, internalizing nucleic acid or tumor-homing nucleic acid is first determined and then one or more nucleotides is replaced by a nucleoside or nucleoside analog. This replacement comprises synthesizing the targeted aptamer, internalizing nucleic acid or tumor-homing nucleic acid and incorporating the nucleoside or nucleoside analog during the synthesis. The synthesis may be done by any method known in the art, such as chemically or enzymatically. Preferably, the incorporation of the nucleoside or nucleoside analog does not compromise the binding ability or specificity of the targeted aptamer, internalizing nucleic acid or tumor-homing nucleic acid.

In the direct selection method, first a naïve combinatorial aptamer, internalizing nucleic acid or tumor-homing nucleic acid prodrug library is prepared. This naïve combinatorial aptamer, internalizing nucleic acid or tumor-homing nucleic acid prodrug library contains a large number ($10^{14}$-$10^{15}$) of aptamer, internalizing nucleic acid or tumor-homing nucleic acid candidates. A naïve combinatorial aptamer, internalizing nucleic acid or tumor-homing nucleic acid prodrug library can be prepared by any method known in the art. For example, aptamer, internalizing nucleic acid or tumor-homing nucleic acid prodrugs can be prepared by hybridizing oligonucleotides, or incorporating nucleoside or nucleoside analog into a selection of aptamer, internalizing nucleic acid or tumor-homing nucleic acids. The aptamer, internalizing nucleic acid or tumor-homing nucleic acids themselves may be selected by any method known in the art, for example an existing naïve combinatorial library of aptamer, internalizing nucleic acid or tumor-homing nucleic acids or any other group of aptamer, internalizing nucleic acid or tumor-homing nucleic acids, whether completely randomly generated or otherwise. The aptamer, internalizing nucleic acid or tumor-homing nucleic acids may be hybridized with oligonucleotides or have nucleosides or nucleoside analogs incorporated within. The nucleoside or nucleoside analog maybe incorporated within the aptamer, internalizing nucleic acid or tumor-homing nucleic acid by any method known in the art including replacing one or more nucleotides during transcription or synthesis. The aptamer, internalizing nucleic acid or tumor-homing nucleic acid candidates in the naïve combinatorial aptamer, internalizing nucleic acid or tumor-homing nucleic acid prodrug library may be modified versions of any aptamer, internalizing nucleic acid or tumor-homing nucleic acid library known in the art, such as those used in SELEX. Alternatively, the aptamer, internalizing nucleic acid or tumor-homing nucleic acid candidates in the naïve combinatorial prodrug library may be created de novo. Once the naïve combinatorial aptamer, internalizing nucleic acid or tumor-homing nucleic acid prodrug library is prepared, iterative rounds of selection are run to determine the aptamer, internalizing nucleic acid or tumor-homing nucleic acid prodrug targeting the cells in question.

Iterative rounds of selection maybe done by any method known in the art. This includes, but is not limited to, in vitro SELEX, whole-body SELEX, in vitro selection for internalization by the cells, or whole-body selection for internalization by the cells.

The subject may be any subject. Preferably, the subject is a mammal. More preferably, the subject is a human.

The cells may be any cells from any tissue in the subject including but not limited to, blood, skeletal, breast, cardiac, neural, renal, pancreatic, gastric, liver, splenic, muscle, or pulmonary tissue. The cells may be normal, diseased, cancerous or may be infected with a virus or other pathogen.

The present invention provides the oligonucleotide, nucleoside or nucleoside analog prepared for selective introduction in a subject's cells by (1) selecting a targeted aptamer, internalizing nucleic acid or tumor-homing nucleic acid via iterative rounds of selection, and hybridizing an oligonucleotide to the targeted aptamer, internalizing nucleic acid or tumor-homing nucleic acid; (2) selecting a targeted aptamer, internalizing nucleic acid or tumor-homing nucleic acid via iterative rounds of selection, and replacing one or more nucleotide with a nucleoside or nucleoside analog; (3) selecting a targeted aptamer, internalizing nucleic acid or tumor-homing nucleic acid via iterative rounds of selection, and synthesizing the targeted aptamer, internalizing nucleic acid or tumor-homing nucleic acid with one or more nucleoside or nucleoside aptamer, internalizing nucleic acid or tumor-homing nucleic acids; or (4) preparing a naïve combinatorial aptamer, internalizing nucleic acid or tumor-homing nucleic acid prodrug library, and running iterative rounds of selection for the cells. For example, the oligonucleotide, nucleoside or nucleoside analog prepared for selective introduction in a subject's cells may be the oligonucleotide, nucleoside or nucleoside analog of SEQ ID NO:9, SEQ ID NO:10, or SEQ ID NO:6 hybridized to SEQ ID NO:7.

The present invention additionally provides an oligonucleotide, nucleoside or nucleoside analog prepared for selective introduction into a subject's cells of SEQ ID NOS:9 or 10 or SEQ ID NO:6 hybridized to SEQ ID NO:7.

The aptamer prodrugs of SEQ ID NOS:9 and 10 were generated by site specific incorporation of floxuridine (5FdU) during synthesis of the known aptamer scgc.8. AU*CU*AACU*GCTGCGCCGCCGGGAAAA TACTGTACGGU*U*AGA (SEQ ID NO:9); AU*CU*AACU*GCU*GCGCCGCCGGGAAAA U*ACU*GU*ACGGU*U*AGA (SEQ ID NO:10). U* denotes 5FdU.

The aptamer of SEQ ID NO:6 has the sequence GGGGGATCAATCCGGCTACCCCGTG-TAACGTCTAGCCACACCCCGAATTAAATG CCCGC-CATGACCAG (SEQ ID NO:6). SEQ. ID NO:6 was generated by adding a hybridization handle to c2m9.1 which has the sequence GGGGGATCAATCCGGCTACCCCGTG-TAACGTCTAGCCACACCCC (SEQ ID NO:5). The minimized aptamer of SEQ ID NO:5 was generated from Clone 2-GGGAGGTGAATGGTTCTACGATTCAAACATCT-CACAGATCAATCCAAGGGACCT CGTTAAAGGAC-GACTCCCTTACATGCGAGATGACCACGTAAGGAAT-TAAATGC CCGCCATGACCAG (SEQ ID NO:1) and clone 11-GGGAGGTGAATGGTTCTACGATCATTACG-GCTACCCCGTGTAACGTCTAGCCAA AGTAGTAC-CAAAAGTCAGTTACATGCGAGATGACCACGTAATT-GAATTAAATG CCCGCCATGACCAG (SEQ ID NO:3). An aptamer prodrug can be generated by hybridizing SEQ ID NO:6 to C*TC*C*TC*ATGC*C*GC*GC*ATC*TC*ATTA (SEQ ID NO:7), where C*=5-fluorodeoxycytidine.

The present invention provides a targeted aptamer, internalizing nucleic acid or tumor-homing nucleic acid selected by the method of any of (1) selecting a targeted aptamer, internalizing nucleic acid or tumor-homing nucleic acid via iterative rounds of selection, and hybridizing an oligonucleotide to the targeted aptamer, internalizing nucleic acid or tumor-homing nucleic acid; (2) selecting a targeted aptamer, internalizing nucleic acid or tumor-homing nucleic acid via iterative rounds of selection, and replacing one or more nucleotide with a nucleoside or nucleoside analog; (3) selecting a targeted aptamer, internalizing nucleic acid or tumor-homing nucleic acid via iterative rounds of selection, and synthesizing the targeted aptamer, internalizing nucleic acid or tumor-homing nucleic acid with one or more nucleoside or nucleoside aptamer, internalizing nucleic acid or tumor-homing nucleic acids; or (4) preparing a naïve combinatorial aptamer, internalizing nucleic acid or tumor-homing nucleic acid prodrug library, and running iterative rounds of selection for the cells, wherein the targeted aptamer, internalizing nucleic acid or tumor-homing nucleic acid comprises the targeted aptamer, internalizing nucleic acid or tumor-homing nucleic acid of SEQ ID NOS: 1, 2, 3, 4, 5, 6, 11 or 12.

The present invention further provides a targeted aptamer, internalizing nucleic acid or tumor-homing nucleic acid of SEQ ID NOS: 1, 2, 3, 4, 5, 6, 11 or 12.

The aptamers of SEQ ID NOS: 1, 2, and 3 were generated from a 2'F modified RNA pool containing a 50 nucleotide random sequence core flanked by primer binding sites. They are labeled clones 2, 4, and 11. Clone 2-GGGAGGT-GAATGGTTCTACGATTCAAACATCTCACAGAT-CAATCCAAGGGACCT CGTTAAAGGACGACTCCCT-TACATGCGAGATGACCACGTAAGGAATTAAATGC CCGCCATGACCAG (SEQ ID NO:1) clone 4-GGGAGGT-GAATGGTTCTACGATTAGGTTAGCGGCAGATCAC-TACAAAGCCCCT AGAGCACATGCTCCACCGCTTTA-CATGCCGAGATGACCACCGTAATAGAATTAA ATGCCCGCCATGACCAG (SEQ ID NO:2); clone 11-GGGAGGTGAATGGTTCTACGATCATTACGGC-TACCCCGTGTAACGTCTAGCCAA AGTAGTAC-CAAAAGTCAGTTACATGCGAGATGACCACGTAATT-GAATTAAATG CCCGCCATGACCAG (SEQ ID NO:3). The minimized aptamer of SEQ ID NO:4 was generated from clone 2. C2m8: GGGGGATCAATCCAAGGGAC-CCGGAAACGCTCCCTTACACCCC (SEQ ID NO:4). The minimized aptamer of SEQ ID NO:5 was generated from clone 2 and 11. C2m9.1: GGGGGATCAATCCGGCTAC-CCCGTGTAACGTCTAGCCACACCCC (SEQ ID NO:5). The aptamer of SEQ ID NO:6 was generated by adding a hybridization handle to c2m9.1. GGGGGATCAATCCG-GCTACCCCGTGTAACGTCTAGCCACACCCCGAAT-TAAATG CCCGCCATGACCAG (SEQ ID NO:6).

The internalizing nucleic acid of SEQ ID NO:11 was generated from a 2'F modified RNA library containing 50 nucleotide random sequence core flanked by primer binding sites. GGGAGGUGAAUGGUUCUACGAUAUUGC-GAAUCCUCUAUCCGUUCUAAACGCU UUAUGAUUUCGCAUAGUCCUUACAUGCGA-GAUGACCACCGUAAUUGAAUUAA AUGCCCGC-CAUGACCAG (SEQ ID NO:11). SEQ ID NO:12 is the minimized core of SEQ ID NO:11. UGCGAAUCCUC-UAUCCGUUCUAAACGCUUUAUGAUUUCGCA (SEQ ID NO:12).

The present invention additionally provides a pharmaceutical composition comprising a therapeutically effective amount of the aptamer, internalizing nucleic acid, or tumor-homing nucleic acid comprising the oligonucleotide, nucleoside or nucleoside analog prepared for selective introduction in a subject's cells in a pharmaceutically acceptable carrier. The pharmaceutical composition may comprise the aptamer, internalizing nucleic acid, or tumor-homing nucleic acid comprising the oligonucleotide, nucleoside or nucleoside analog prepared for selective introduction in a subject's cells in a pharmaceutically acceptable carrier. Alternatively, the pharmaceutical composition may consist essentially of the aptamer, internalizing nucleic acid, or tumor-homing nucleic acid comprising the oligonucleotide, nucleoside or nucleoside analog prepared for selective introduction in a subject's cells in a pharmaceutically acceptable carrier, i.e. having no other pharmaceutically active ingredients. Yet alternatively, the pharmaceutical composition may consist of the aptamer, internalizing nucleic acid, or tumor-homing nucleic acid comprising the oligonucleotide, nucleoside or nucleoside analog prepared for selective introduction in a subject's cells in a pharmaceutically acceptable carrier.

The pharmaceutically acceptable carrier must be compatible with the aptamer, internalizing nucleic acid, or tumor-homing nucleic acid comprising the oligonucleotide, nucleoside or nucleoside analog prepared for selective introduction in a subject's cells, and not deleterious to the subject. Examples of acceptable pharmaceutical carriers include carboxymethylcellulose, crystalline cellulose, glycerin, gum arabic, lactose, magnesium stearate, methylcellulose, powders, saline, sodium alginate, sucrose, starch, talc, and water, among others. Formulations of the pharmaceutical composition may conveniently be presented in unit dosage and may be prepared by any method known in the pharmaceutical art. For example, the aptamer, internalizing nucleic acid, or tumor-homing nucleic acid comprising the oligonucleotide, nucleoside or nucleoside analog prepared for selective introduction in a subject's cells may be brought into association with a carrier or diluent, as a suspension or solution. Optionally, one or more accessory ingredients, such as buffers, flavoring agents, surface-active ingredients, and the like, may also be added. The choice of carriers will depend on the method of administration. The pharmaceutical composition can be formulated for administration by any method known in the art, including but not limited to, intravenously and orally. The pharmaceutical composition would be useful for administering the aptamer, internalizing nucleic acid, or tumor-homing nucleic acid comprising the oligonucleotide, nucleoside or nucleoside analog prepared for selective introduction in a subject's cells to a subject to prevent or treat cancer or to prevent or treat viral infection. The aptamer, internalizing nucleic acid, or tumor-homing nucleic acid comprising the oligonucleotide, nucleoside or nucleoside analog prepared for selective introduction in a subject's cells is provided in amounts effective to prevent or treat cancer or to prevent or treat viral infection in the subject's cells. These amounts may be readily determined by one of a variety of standard pharmacological approaches. In one embodiment, the aptamer, internalizing nucleic acid, or tumor-homing nucleic acid comprising the oligonucleotide, nucleoside or nucleoside analog prepared for selective introduction in a subject's cells is the sole active pharmaceutical ingredient in the formulation or composition. In another embodiment, there may be a number of active pharmaceutical ingredients in the formulation or composition aside from the aptamer, internalizing nucleic acid, or tumor-homing nucleic acid comprising the oligonucleotide, nucleoside or nucleoside analog prepared for selective introduction in a subject's cells. In this embodiment, the other active pharmaceutical ingredients in the formulation or composition must be compatible with the aptamer, internalizing nucleic acid, or tumor-homing nucleic acid comprising the oligonucleotide, nucleoside or nucleoside analog prepared for selective introduction in a subject's cells.

The present invention further provides a method of protecting a subject from, or treating a subject with, cancer or viral infection, the method comprising administering to the subject a therapeutically effective amount of an aptamer, internalizing nucleic acid, or tumor-homing nucleic acid comprising the oligonucleotide, nucleoside or nucleoside analog prepared for selective introduction in a subject's cells or a pharmaceutical composition thereof.

As used herein, "protecting" a subject from cancer, or grammatical equivalent thereof, means forestalling clinically significant tumorigenesis of cancer. As used herein, "treating" a subject's cancer, or grammatical equivalent thereof, means effecting a clinically significant reduction in tumorigenesis of cancer.

As used herein, "protecting" a subject from viral infection, or grammatical equivalent thereof, means preventing primary or secondary infection of the subject's cells by a virus. A primary infection is when a virus infects the first cell. A secondary infection is when virus, created inside of and released from the first cell, infects additional cells. As used herein, "treating" a subject with viral infection, or grammatical equivalent thereof, means effecting a clinically significant reduction in the subject's viral load and/or the number of infected cells in the subject.

In an embodiment the aptamer, internalizing nucleic acid, or tumor-homing nucleic acid comprising the oligonucleotide, nucleoside or nucleoside analog prepared for selective introduction in a subject's cells comprises residues having the sequence SEQ ID NO:9, SEQ ID NO:10, or SEQ ID NO:6 hybridized to SEQ ID NO:7 or an analog thereof differing by having one or more nucleoside analogs inserted therein, substituted therein, or added thereto.

The present invention additionally provides the use of an oligonucleotide, nucleoside or nucleoside analog prepared for selective introduction in a subject's cells to protect or treat the subject from cancer or viral infection. For example, the oligonucleotide, nucleoside or nucleoside analog prepared for selective introduction in a subject's cells may be the oligonucleotide, nucleoside or nucleoside analog of SEQ ID NO:9, SEQ ID NO:10, or SEQ ID NO:6 hybridized to SEQ ID NO:7.

All combinations of the various elements described herein are within the scope of the invention unless otherwise indicated herein or otherwise clearly contradicted by context.

Where a numerical range is provided herein, it is understood that all numerical subsets of that range, and all the individual integers contained therein, are provided as part of the invention. Thus, for example, an oligonucleotide which is from 5 to 25 nucleotides in length includes the subset of oligonucleotides which are 18 to 22 nucleotides in length, the subset of oligonucleotides which are 20 to 25 nucleotides in length etc. as well as a oligonucleotide which is 5 nucleotides in length, a oligonucleotide which is 6 nucleotides in length, a oligonucleotide which is 7 nucleotides in length, etc. up to and including a oligonucleotide which is 25 nucleotides in length.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Using an aptamer that targets the human transferrin receptor (CD71) that was developed and which robustly binds CD71 and is readily internalized by a variety of different cancer cell lines, four approaches have been tested for developing the aptamer into prodrugs. Results from these approaches are reported here for: a) drug incorporation via hybridization of drug-laden sequences to the aptamer, b)

direct incorporation of the drugs via transcription into existing aptamers, and c) direct incorporation of the drug by chemical synthesis. In addition, methods have been developed to identify aptamers that target and are specifically internalized by cells without prior knowledge of surface receptors.

Drug Incorporation Via Hybridization

Because they are nucleic acids, a simple method for attaching functional nucleoside analog drugs to aptamers is via hybridization of drug-laden sequences to the aptamer. Indeed, hybridization is routinely utilized to label aptamers and aptamer libraries for FACS analysis, and a similar approach has previously been used for appending siRNA to aptamers (McNamara et al. 2006; Zhou et al. 2008).

To test the feasibility of this strategy for delivery of nucleoside analog drugs, two different anti-hTfR aptamers (designated min8 and min9.1) were extended with a 24 nucleotide extension. A complementary DNA oligonucleotide (FdC-oligo) was then synthesized to this region in which all cytosine residues had been replaced with the nucleoside analog 5F-deoxycytidine (FdC), a potent inhibitor of methyltransferase activity (Beumer et al. 2008). The aptamer-produgs were then assembled by mixing the drug oligo at a 1:1 molar ratio with one of two different minized anti-hTfR aptamers, min8, min9.1, or a non-targeting control aptamer (cntrl) in PBS and thermally equilibrated by heating at 70.degree. C. Aptamer function following hybridization was confirmed by FACS using a FITC labeled version of the oligonucleotide.

Figure 3:
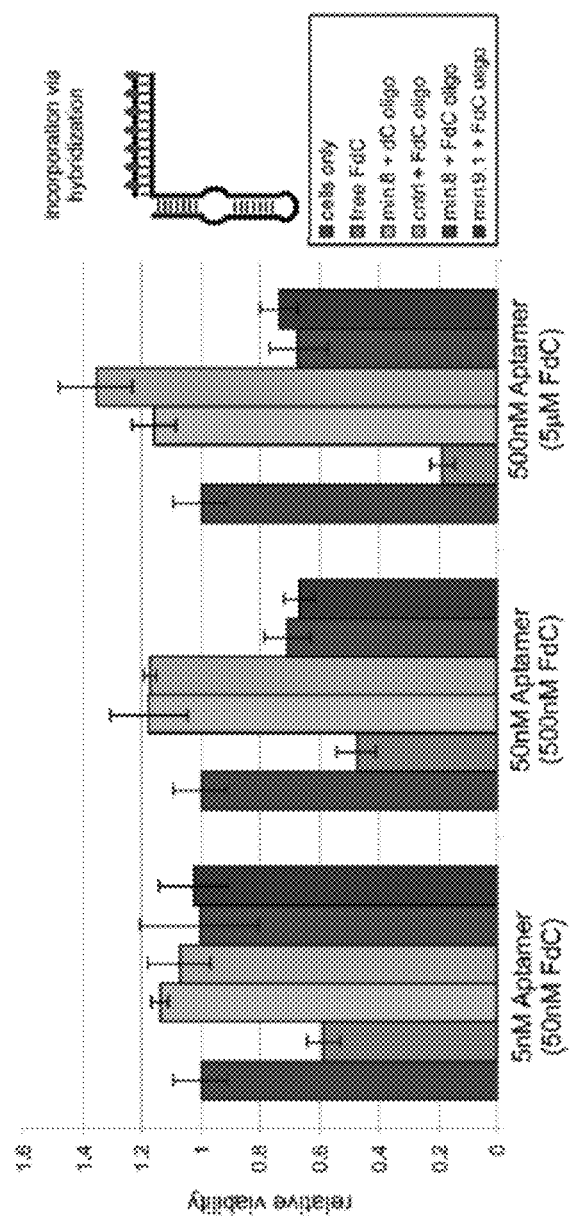
FIG. 3. Relative viability of cells after varying dosage of aptamer, internalizing nucleic acid or tumor-homing nucleic acid prodrugs and free drug.

The ability of the assembled anti-hTfR aptamer-prodrugs to deliver therapeutic cargo to cells was tested on HeLa cells. To avoid potential complications from degradation of the FdC-oligo (which is DNA and thus readily susceptible to degradation), these assays were performed in serum free media (DMEM containing 1% Nutridoma). Cells were incubated with increasing concentrations of either free drug, anti-hTfR aptamer-prodrugs or controls for 4 days, after which cell viability was assayed using the chromogenic substrate alamarBlue. As shown in FIG. 3, at 50 nM aptamer the loss of cell viability was only observed for cells treated with the free drug (FIG. 3), or the two anti-hTfR aptamer-prodrugs (FIG. 3). Importantly, no effect on cell health was observed when cells were exposed to a non-targeting control aptamer-prodrug (FIG. 3) or an anti-hTfR aptamer hybridized to non-drug containing oligonucleotide (FIG. 3), indicating that the loss of viability was not due to degradation of the FdC-oligo in the media or from binding of the anti-hTfR aptamers. The lack of activity at 5 nM is consistent with the lower levels (~10-fold) of fluorescent staining seen when binding assays are performed at this concentration. Similarly, the lack of improvement in the toxicity observed at 500 nM aptamer is consistent with saturation of the surface receptor. Clearly, delivery of nucleoside analog drugs specifically to hTfR-expressing cells can be effected by hybridization of a drug-laden oligo to the targeting aptamer.

Drug Incorporation Via Transcription

Previous reports have demonstrated that in some cases a single nucleotide within an aptamer can be replaced with another. For example, Alder et al. generated nuclease stable anti-trypanisome aptamers by replaing the natural 2'OH bearing C and U residues with 2'-F-dC and dU (Adler et al. 2008). Similarly, the 2'F pyrimidines in a nuclease stabilized anti-osteopontin aptamer could be replaced with 2'OMe pyrimidines (Mi et al. 2009). To investigate this possibility, aptamers c2, c4 and c11 have been transcribed using two different sets of nucleotide mixtures: one in which ATP was replaced with the anti-metabolite 7-deaza-ATP (tubercidin), and one in which 2'F UTP was replaced with 5-fluorodeoxyUTP (floxuridine). Both of these nucleoside analogs were efficiently incorporated by the T7 RNA polymerase mutant Y639F, which is routinely used to generate modified RNA. This ability to readily incorporate these drugs via transcription bodes well for the ability to produce drug-laden aptamers. Additionally, aptamers can be generated from random libraries containing a nucleoside drug analog. The drug constructs are then tested to ensure that incorporation of the analogs has not hampered the aptamers' binding ability.

Drug Incorporation by Chemical Synthesis

Figures 4A, 4B:
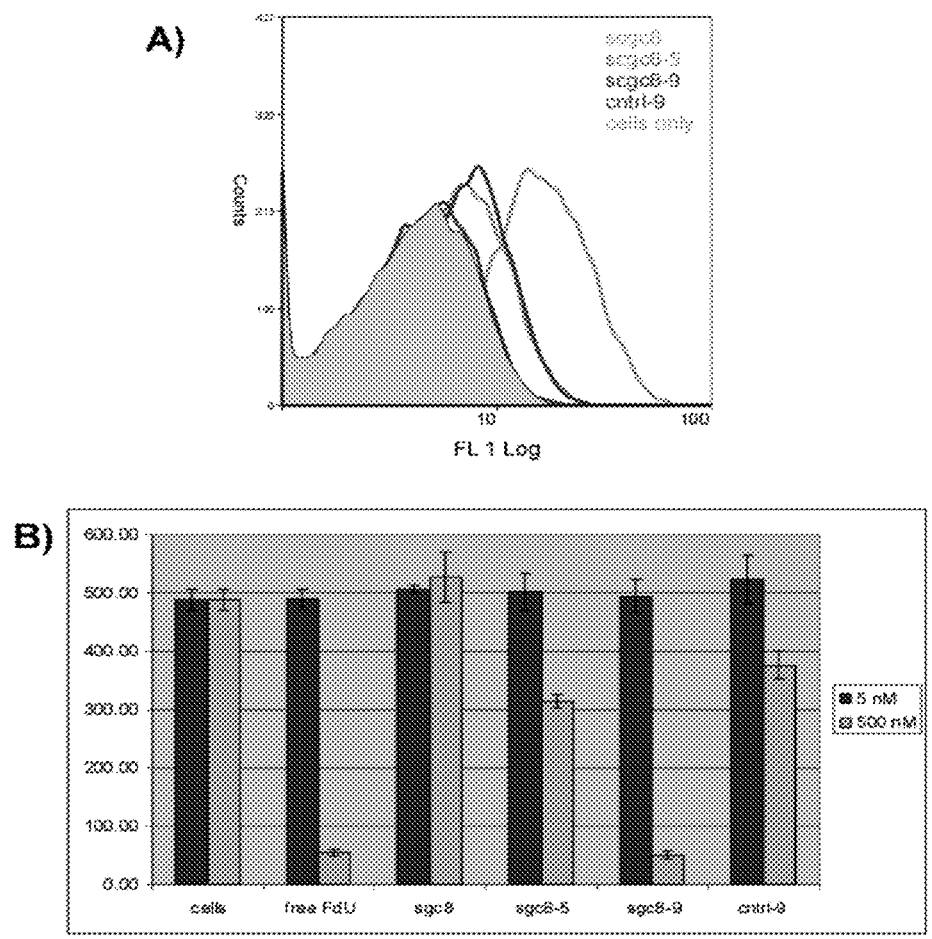
FIG. 4A-4B. Drug incorporation by chemical synthesis. (4A) Binding efficiency of aptamer, internalizing nucleic acid or tumor-homing nucleic acids prodrugs (scgc8-5, scgc8-9) compared to scrambled control sequence (cntrl-9) and non-drug containing aptamer, non-drug internalizing nucleic acid or non-drug tumor-homing nucleic acid (scgc8-5). (4B) Toxicity levels of free drug and stabilize aptamer, internalizing nucleic acid or tumor-homing nucleic acid prodrugs.

In addition to adding drugs to aptamers by hybridization, a series of aptamer-prodrugs has been synthesized using a DNA aptamer (scgc8) which targets human protein tyrosine kinase-7. This protein is overexpressed on a variety of leukemia cell lines, and aptamer scgc8 has been shown to be endocytosed by cells expressing this protein (Xiao et al. 2008). As shown in FIG. 4A, fluorescently labeled aptamers synthesized in which 5 of 9 (scgc8-5) or all 9 (scgc8-9) thymidine residues were replaced with floxuridine still bound target cells better than a scrambled control sequence (cntrl-9) but less efficiently than the non-drug containing aptamer (scgc8). To stabilize these aptamers against serum nucleases, the oligonucleotides were generated bearing a 3' inverted thymidine residue which dramatically stabilizes the serum half-life of DNA molecules to ~20 hrs (Dass et al. 2002). Importantly, when these same constructs were incubated with Jurkat cells grown in regular media (RPMI+10% FBS) at a concentration of 500 nM, scgc8-9 inhibited cell growth as efficiently as free drug alone, while both scgc8-5, which contains fewer drug molecules and cntrl-9 which does not bind these cells showed considerable lower levels of toxicity (FIG. 4B).

Development of New Methods for Targeting Cell with Aptamers and Generating Targeted Prodrugs The most recent work has been focused on identifying aptamers which target beta cells for both the treatment and diagnosis of diabetes. The methods are highly relevant to the development of targeted pro-drugs, and are a testament to the core competency in developing reagents which can target cells without prior knowledge of specific molecule surface targets.

Aptamers that target and are internalized by beta cells were identified by performing an internalization selection against the glucose-responsive immortalized mouse beta cell line Min6B1. As in the selection against the transferrin receptor described above, in order to drive the selection towards molecules that are internalized, following incubation with the RNA library, target cells were washed extensively and treated with trypsin and ribonuclease to remove any surface bound RNA. Following recovery of total RNA, aptamers were amplified, transcribed and the process was repeated. The dominant clone identified in the selection is readily internalized by Min6B1 cells. However, the most recent results suggest that this aptamer is not specific for beta cells. Interestingly, it seems to be internalized by almost all cells upon which it has been tested, including human cell lines.

Most recently, a modified version of a tissue culture-based selection methodology has been applied to whole animal models. Similar approaches have already been successfully applied to identify peptides which bind vascular targets using phage display (Trepel et al. 2008). However, those approaches are likely hampered by the large size of the phage (~1 μm×10 nm, mw~105 KDa) which greatly limits extravasation. The much smaller size of aptamers (MW≤~40

Figure 5:
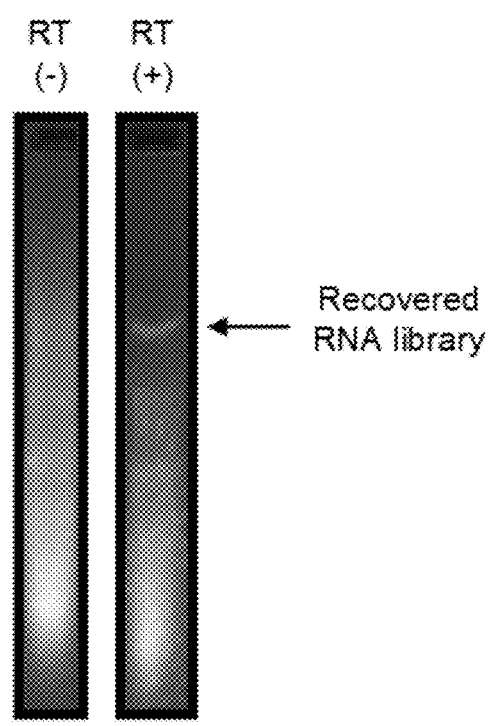
FIG. 5. PCR of RNA library recovered from a mouse pancreas following i.v. tail vein injection. RT(+) contains reverse transciptase.

KDa) makes them more ideal for identifying reagents that can not only extravasate but also internalize into cancer cells in vivo. In this way, it may be possible to identity RNA ligands that directly target tumors and/or diseased tissue directly in live animals. To this end, experiments have been performed to test whether RNA libraries could be recovered at specific sites following injection into whole animals. A rat was injected with 100 µg of a nuclease stabilized RNA library. Two hours later, the rat was sacrificed, the pancreas was removed, and total RNA from that organ was recovered. As shown in FIG. 5, the injected library could be specifically amplified from the pancreatic RNA. Thus, the ability to recover rounds of selection was demonstrated, potentiating the transition of the cell selection protocol to whole animals (whole animal SELEX).

Recent work from the Sullenger Lab at Duke University has demonstrated that the in vivo selection methodology is indeed a viable route to identifying nucleic acids which localize to tumors. By injecting mice bearing tumors, they were able to isolate two classes of RNA molecules that localize to and are taken up by tumors (Mi et al. 2010). Building on the technologies established above, cell internalization selections as well as tumor-homing selections can be taken even further. By generating libraries of nucleic acids composed of nucleoside analogs, cell and tumor-homing pro-drugs can be directly selected for. Libraries containing the nucleoside analog drug 5-fluorouridine, an FDA approved drug, and 7 deazaadenosine, an anti-metabolite, are being generated, with plans to use them both for cell internalization selections and tumor-homing selection.

EXAMPLES

1. Transferrin Receptor (CD71)

Aptamers that target the human transferrin receptor, CD71, were generated in lab from a 2'F modified RNA pool containing a 50 nucleotide random sequence core flanked by primer binding sites. Four rounds of in vitro selection were carried out using recombinant HIS-tagged human transferrin receptor produced from insect cells. Following the fourth round of selection, an 'internalization selection' was performed using HeLa cells, a human cervical cancer cell line known to express TfR. HeLa cells were incubated with the fourth round aptamer library in media for an hour and then extensively washed and treated with trypsin and ribonucleases to remove any cell surface-bound RNA. Following stringent washing, Trizol® was used to extract total RNA from the cells, recovering any aptamers that had been internalized by the cells and thus protected from nuclease treatment. While the fourth round population showed little to no ability to bind to Jurkat cells, a human T cell line also known to express the transferrin receptor, the fifth round population showed strong binding. Sequence analysis of the population yielded three functional clones from the population which were of independent origin, but share the same core structural motif.

The sequence of these clones are: clone 2: GGGAGGTGAATGGTTCTACGATTCAAACATCTC ACAGATCAATCCAAGGGACCT CGTTAAAGGAC-GACTCCC TTACATGCGAGATGACCACGTAAGGAATTAAATGC CCGCCATGACCAG (SEQ ID NO:1); clone 4: GGGAGGTGAATGGTTCTACGATTAGGTTAGCGG CAGATCACTACAAAGCCCCT AGAGCACATGCTC-CACCGCT TTACATGCCGAGATGACCACCGTAATAGAATTA AATGCCCGCCATGACCAG (SEQ ID NO:2); clone 11: GGGAGGTGAATGGTTCTACGATCATTACG GCTAC-CCCGTGTAACGTCTAGCCAA AGTAGTAC-CAAAAGTCAG TTACATGCGAGATGACCACGTAATTGAATTAAAT GCCCGCCATGACCAG (SEQ ID NO:3). The underlined regions represent the constant regions used to amplify the library.

Structural analysis of the clones led to the identification of a conserved core motif and allowed for minimization of the aptamer. The sequence of two minimized clones are given below. The first, c2m8, represent a truncation (both 5' and 3') clone 2. The second represents a chimeric aptamer composed of portion of both clone 2 and clone 11. c2m8: GGGGGATCAATCCAAGGGACCCGGAAACGCTC-CCTTACACCCC (SEQ ID NO:4); c2m9.1: GGGGGAT-CAATCCGGCTACCCCGTGTAACGTCTAGCCACAC-CCC (SEQ ID NO:5).

Minimized clones were adapted for prodrug delivery via hybridization. For these experiments the drug 5-fluorodeoxycytidine 5FdC was utilized. For this, the 3' end of a minimized aptamer was extended by PCR to add a hybridization handle. For example:

c2m9.1.drug: GGGGGATCAATCCGGCTACCCCGTG-TAACGTCTAGCCACACCCCGAATTAAATG CCCGC-CATGACCAG (SEQ ID NO:6). The underlined portion is partially complementary to the drug laden oligonucleotide.

A drug laden oligonucleotide, 5FdC.oligo.1, was synthesized by standard solid phase DNA/RNA synthesis in lab. The sequence is: 5FdC.oligo.1 C*TC*C*TC*ATGC*C*GC*GC*ATC*TC*ATTA (SEQ ID NO:7), where C*=5-fluorodeoxycytidine.

The minimized extended aptamer c2m9.1.drug was combined at a 1:1 molar ratio with the drug laden oligonucleotide, 5FdC.oligo.1 in DPBS containing $Ca^{2+}$ and $Mg^{2+}$. The mixture was heated to 70° C. for 3 minutes and then placed on the benchtop at room temperature for a minimum of 15 minutes before use.

2. Protein Kinase 7

A ssDNA aptamer that targets protein kinase 7 was selected by Shanggun et al (J Proteome Res, 2008 7:2133). The aptamer, scgc.8, was adapted for the delivery of floxuridine (5FdU) by site specific incorporation this nucleoside analog drug during chemical synthesis. Aptamer prodrugs were synthesized bearing a 5' fluorescein molecule and a 3' inverted thymiding residue to enhance serum stability. The sequence of the parental aptamer and the aptamer prodrugs are: Scgc.8 ATCTAACTGCTGCGCCGC-CGGGAAAATACTGTACGGTTAGA (SEQ ID NO:8); Scgc.8-5 AU*CU*AACU*GCTGCGCCGCCGGGAAAATAC TGTACGGU*U*AGA (SEQ ID NO:9); Scgc.8-9 AU*CU*AACU*GCU*GCGCCGCCGGGAAAAU* ACU*GU*ACGGU*U*AGA (SEQ ID NO:10). U* denotes 5FdU.

3. Internalizing Aptamer "Clone 1"

Selection Identification and Characterization

Figure 6:
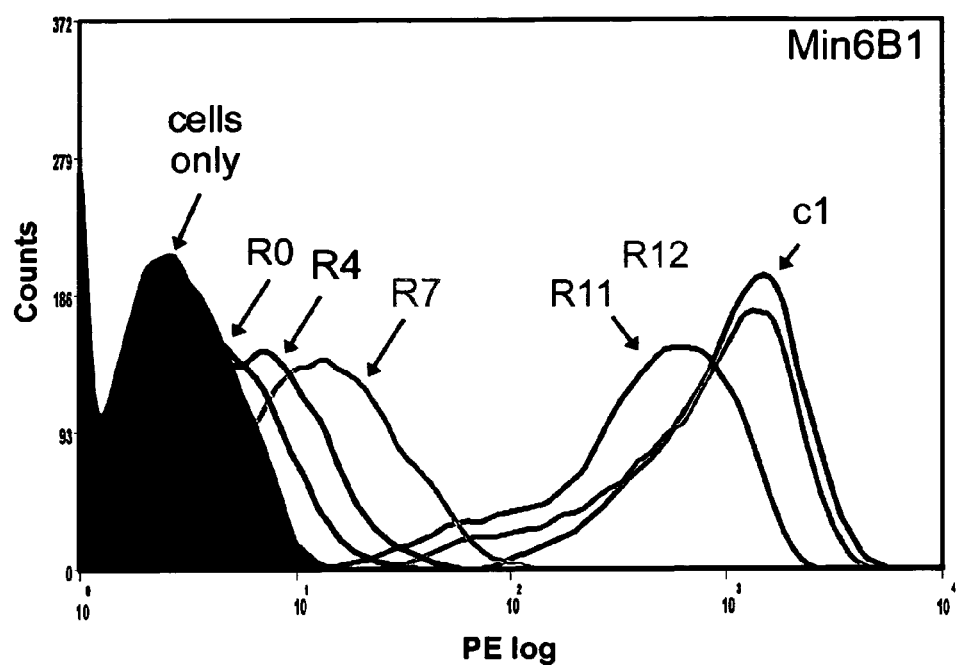
FIG. 6. FACS-based binding assay of individual rounds of selection: Min6B1 cells were incubated with either Round 0 (random library), 4, 7, 11, 12 or clone 1 (C1). Aptamer pools were hybridized with an R-phycoerythrin labeled primer and screened by flow cytometry.

A selection was conducted to identify RNA molecules capable of specifically internalizing into pancreatic beta cells. Min6B1 cells, an immortalized mouse beta cell line, were chosen to be targeted. Selections were conducted using a 2'F modified RNA library containing a 50 nucleotide random sequence core flanked by primer binding sites. For rounds 1 through 6, Min6B1 cells were incubated with the library for 1 hour at 37° C. Following incubation, the cells were washed stringently to remove any non-bound sequences and the cells subsequently lifted by treatment (5 minutes) with trypsin. The cells were then transferred to a 1.5 milliliter microcentrifuge tube, washed an additional time, and the total RNA was recovered by Trizol® extraction. The recovered RNA was reverse transcribed and then amplified by PCR. The double stranded DNA was subsequently converted back into 2'F RNA and used for an additional round of selection. After the 7th round and following trypsinization, extracellular RNAse treatment was introduced to further drive the selection towards the identification of RNA molecules capable of internalizing into cells. For rounds 11 and 12 primary isolated mouse islets were the target for selection. When biotinylated and conjugated to streptavidin phycoerytherin (PE), aptamers from individual rounds of the selection showed significant staining of Min6B1 cells by flow cytometry, with rounds 11 and 12 displaying the highest signals (FIG. 6). Sequence analysis of the Round 12 population revealed one dominant (50%) sequence (clone 1; C1). Consistent with the sequencing data from Round 12, analysis of C1 demonstrated significant cell labeling.

In accordance with the internalization selection strategy, fluorescence microscopy on Min6B1 cells suggested that C1 not only binds to, but is also internalized by this cell type, as can be observed by its punctate pattern of staining. When similar experiments were conducted with the unselected library, little or no fluorescent signal was observed.

Specificity studies were performed with additional mouse (fibroblasts, brain endothelial, skeletal and myocardial muscles) and human (cervical and prostate cancer) cell lines showing that C1 targets several unrelated cell lines across different species. Thus far the selected RNA sequence gets into all cell lines tested, mouse or human and thus may prove useful as a universal transfection/delivery agent. The molecule may also prove useful in altering the pharmickokinetics and dynamics of small molecule drugs.

The sequence of C1 and the minimized core of the aptamer are given below. The minimized aptamer labeled cells as efficiently as the full length clone. C1: GGGAG-GUGAAUGGUUCUACGAUAUUGCGAAUCCUC-UAUCCGUUCUAAACGCU UUAUGAUUUCGCAUA-GUCCUUACAUGCGAGAUGACCACCGUAAUUG AAUUAA AUGCCCGCCAUGACCAG (SEQ ID NO:11). C1.min: UGCGAAUCCUCUAUCCGUUCUAAACGC-UUUAUGAUUUCGCA (SEQ ID NO:12).

Adaptation for Prodrug Delivery

The ability for C1 to enter a variety of different cell types suggest the potential for this molecule to alter the pharmicokinetoics and pharmicodistribution of small molecule drugs. To this end, the ability of substituting nucleotides within this internalizing RNA with the nucleoside analog drugs floxuridine or 7deazaAdenosine was tested. Experiments were conducted with the full length C1 molecule. Drug incorporation was achieved via replacement of 2'FUTP with 5FdUTP or ATP with 7deazaATP during transcription. These nucleosides are well tolerated by mutant T7 RNA polymerases. In lab, a mutant that contains a Y to F mutation at 687 and a P to L mutation at position 266 was used. Following transcription RNAs were purified by denaturing gel electrophoresis. After recovery by precipitation the RNAs were hybridized to a biotinylated oligonucleotide complementary to the 3' end of the constant region of the library and then complexeed with streptavidin-PE. The PE conjugates were incubated with HEK 293 cells grown in suspension at a concentration of 100 nM for 1 hr after which the cells were washed and analyzed by FACS. While replacement with 7-deazaATP abolished the activity of C1, the 5FdUTP substitution was well tolerated. Drug efficacy studies are currently underway in lab.

Discussion

Nucleic acid based ligand molecules, known as aptamers, typically bind their targets with Kd values in the nanomolar to picomolar range and can discriminate between proteins that differ by only a few amino acids (reviewed in (Conrad et al. 1996; Osborne and Ellington 1997)). These macromolecules are also amenable to chemical synthesis which facilitates large scale production and site specific addition of functional groups, thus further abetting modification such as conjugation of therapeutic cargoes (small molecule drugs, toxins) or diagnostic agents. In addition, their small size (~15-30 kDa) allows for rapid clearance and more efficient extravasation and tissue penetration. Importantly, these molecules have thus far proven to be non-toxic, even when delivered to animals at high doses and humans (2003; Chan et al. 2008; DeAnda et al. 1994; Kohn et al. 1999). The first aptamer based drug, Macugen, composed nuclease stabilized RNA containing 2'F pyrimidine residues, was approved by the FDA in 2004, and others are currently in the pipeline (Nimjee et al. 2005).

Aptamers are generated by iterative rounds of in vitro selection, or SELEX. Briefly, randomized pools of RNA or ssDNA are incubated with target molecules under carefully chosen selection conditions. Binding species are partitioned away from non-binders, amplified to generate a new pool, and the process is repeated until a desired 'phenotype' is achieved or until sequence diversity is significantly diminished (FIG. 1).

While aptamers have traditionally been selected against specific soluble proteins or small molecule targets, more recently, the aptamer selection process has advanced to more complex targets such as membrane proteins and even whole cells (Famulok 1999; Guo et al. 2008; Yan et al. 2005). By modifying the composition of the RNA library to contain 2'F pyrimidines instead of 2'OH pyrimidines, the resulting RNA can be rendered largely resistant to serum nucleases, thus providing the opportunity to use these molecules for targeting in cell culture and in vivo. Importantly, this modification has proven to be non-toxic (Apte et al. 2007).

A nuclease stabilized aptamer selected to bind to the prostate specific membrane antigen (PSMA) has been previously utilized to target LNCaP cells, a prostate cancer cell line that overexpresses this marker (Chu et al. 2006a; Chu et al. 2006b; Farokhzad et al. 2004; McNamara et al. 2006). By conjugating an anti-PSMA aptamer to the ribosomal toxin gelonin, which lacks the ability to enter cells and displays low toxicity (IC50~5 µM), it was shown that toxicity was significantly increased (IC50 of ~30 nM) demonstrating the aptamer's ability to escort the toxin into cells. Similarly, this anti-PSMA aptamer has previously been used for delivery of siRNA (Chu et al. 2006b). As with the gelonin conjugates, the aptamer-siRNA conjugates could be added directly to cells in culture media and was specific for cells that expressed PSMA. Others have also used aptamers to delivery siRNA to cells. McNamara et al. utilized a different anti-PSMA aptamer to demonstrate targeted delivery of siRNA to PSMA-positive cells both in tissue culture as well as in tumor bearing mice (McNamara et al. 2006) and Zhou et al. demonstrated the ability to target to cells expressing the HIV-1 glycoprotein GP120 (Zhou et al. 2008).

Aptamers have also now been used for delivery of small molecule drugs. For example, aptamers targeting cell surface receptors have been linked to hydrophobic nanoparticles loaded with drugs such as cisplatin and dotaxel (Dhar et al. 2008; Zhang et al. 2007). Additionally, the drug doxorubicin has been shown to effectively intercalate into an anti-PSMA aptamer thus facilitating delivery to prostate cancer cells expressing this receptor (Bagalkot et al. 2007). Most, recently, Huang et al. chemically conjugated the same drug to a DNA aptamer via an acid labile linker and demonstrated targeted delivery of this anti-tumor agent to the acute lymphoblastic leukemia line CCRF-CEM (Huang et al. 2009). Importantly, toxicity was only observed in cells expressing the target receptor.

Thus, aptamers can be directly conjugated to the same range of therapeutic cargoes as antibodies, and as described above, aptamers may be a superior choice owing largely to its non-immunogenic nature, the ability to precisely control the site of conjugation, and the capacity to chemically produce large quantities of materials.

Among the many cancer drugs currently utilized to treat the multiple forms of this disease exists a class of drugs that are characterized as nucleic acid antagonists. These nucleoside analogs function by interfering with a variety of cellular processes. In particular, many are ultimately incorporated into cellular DNA, RNA (or both) and can lead to strand termination during replication, inhibition of mismatch repair systems or inhibition of methyltransferase function resulting in epigenetic changes in the cell (Ewald et al. 2008). In the present invention, cell surface targeting aptamers will be composed directly of nucleoside analog drugs to specifically target and kill cancerous cells. The resulting 'aptamer prodrugs' will be both ligand and drug, limiting drug distribution in surrounding tissues while maintaining or even enhancing the efficacy of these drugs.

Figure 2:
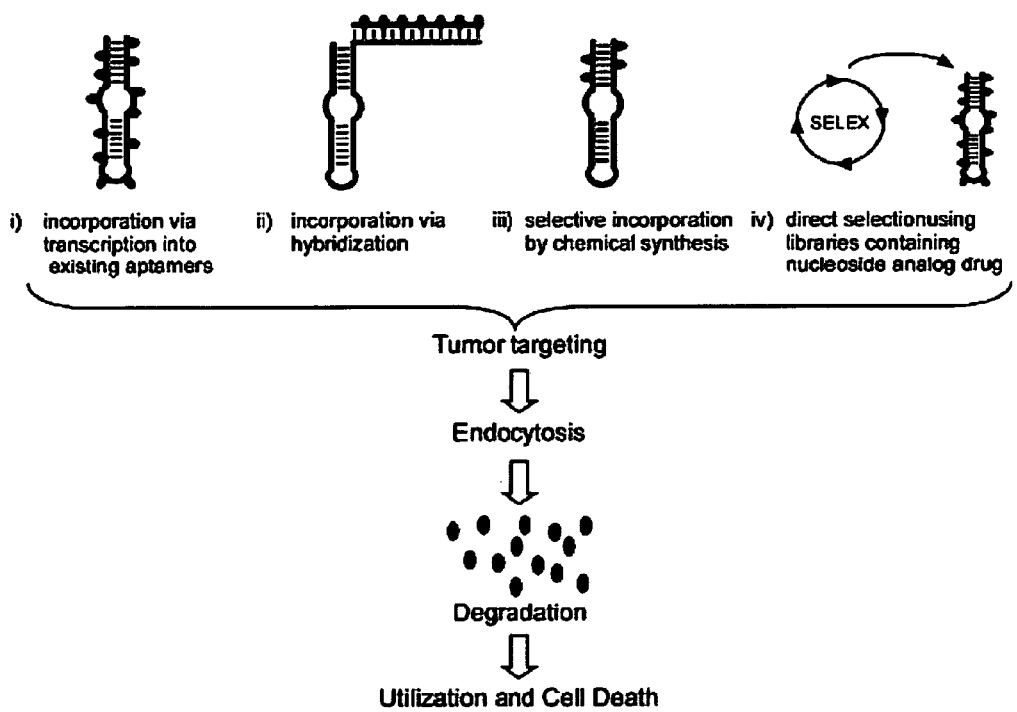
FIG. 2. Four methods of developing aptamer, internalizing nucleic acid or tumor-homing nucleic acid prodrugs composed of nucleoside analog drugs.

There are four main methods of manufacturing 'aptamer-prodrugs' composed of nucleoside analog drugs (FIG. 2). These are: i) incorporation via transcription into existing aptamers, ii) incorporation via hybridization, iii) selective incorporation by chemical synthesis, and iv) direct selection of aptamers from random libraries containing a nucleoside drug analog. In all cases, it is expected that the aptamer-prodrugs will bind cells, be internalized and subsequently be degraded (FIG. 2). Combining this novel approach to drug delivery with novel methods to optimize and select for aptamers which home to tumors, results in a powerful, adaptable drug delivery system that is significantly non-toxic to non-target sites.

REFERENCES 1. (2003) Anti-vascular endothelial growth factor therapy for subfoveal choroidal neovascularization secondary to age-related macular degeneration: phase II study results. Ophthalmology 110:979-86
2. Adler A, Forster N, Homann M, Goringer H U (2008) Post-SELEX chemical optimization of a trypanosome-specific RNA aptamer. Comb Chem High Throughput Screen 11:16-23
3. Apte R S, Modi M, Masonson H, Patel M, Whitfield L, Adamis A P (2007) Pegaptanib 1-year systemic safety results from a safety-pharmacokinetic trial in patients with neovascular age-related macular degeneration. Ophthalmology 114:1702-12
4. Bagalkot V, Zhang L, Levy-Nissenbaum E, Jon S, Kantoff P W, Langer R, Farokhzad O C (2007) Quantum dot-aptamer conjugates for synchronous cancer imaging, therapy, and sensing of drug delivery based on bi-fluorescence resonance energy transfer. Nano Lett 7:3065-70
5. Beumer J H, Parise R A, Newman E M, Doroshow J H, Synold T W, Lenz H J, Egorin M J (2008) Concentrations of the DNA methyltransferase inhibitor 5-fluoro-2'-deoxycytidine (FdCyd) and its cytotoxic metabolites in plasma of patients treated with FdCyd and tetrahydrouridine (THU). Cancer Chemother Pharmacol 62:363-8
6. Carter P J, Senter P D (2008) Antibody-drug conjugates for cancer therapy. Cancer J 14:154-69
7. Chan M Y, Cohen M G, Dyke C K, Myles S K, Aberle L G, Lin M, Walder J, Steinhubl S R, Gilchrist I C, Kleiman N S, Vorchheimer D A, Chronos N, Melloni C, Alexander J H, Harrington R A, Tonkens R M, Becker R C, Rusconi C P (2008) Phase 1b randomized study of antidote-controlled modulation of factor IXa activity in patients with stable coronary artery disease. Circulation 117:2865-74
8. Chu T C, Marks J W, 3rd, Layery L A, Faulkner S, Rosenblum M G, Ellington A D, Levy M (2006a) Aptamer:toxin conjugates that specifically target prostate tumor cells. Cancer Res 66:5989-92
9. Chu T C, Twu K Y, Ellington A D, Levy M (2006b) Aptamer mediated siRNA delivery. Nucleic Acids Res 34:e73
10. Conrad R C, Giver L, Tian Y, Ellington A D (1996) In vitro selection of nucleic acid aptamers that bind proteins. Methods Enzymol 267:336-67
11. Dass C R, Saravolac E G, Li Y, Sun L Q (2002) Cellular uptake, distribution, and stability of 10-23 deoxyribozymes. Antisense Nucleic Acid Drug Dev 12:289-99
12. DeAnda A, Jr., Coutre S E, Moon M R, Vial C M, Griffin L C, Law V S, Komeda M, Leung L L, Miller D C (1994) Pilot study of the efficacy of a thrombin inhibitor for use during cardiopulmonary bypass. Ann Thorac Surg 58:344-50
13. Dhar S, Gu F X, Langer R, Farokhzad O C, Lippard S J (2008) Targeted delivery of cisplatin to prostate cancer cells by aptamer functionalized Pt(IV) prodrug-PLGA-PEG nanoparticles. Proc Natl Acad Sci USA 105:17356-61
14. Ewald B, Sampath D, Plunkett W (2008) Nucleoside analogs: molecular mechanisms signaling cell death. Oncogene 27:6522-37
15. Famulok M (1999) Oligonucleotide aptamers that recognize small molecules. Curr Opin Struct Biol 9:324-9
16. Farokhzad O C, Jon S, Khademhosseini A, Tran T N, Lavan D A, Langer R (2004) Nanoparticle-aptamer bioconjugates: a new approach for targeting prostate cancer cells. Cancer Res 64:7668-72
17. Guo K T, Paul A, Schichor C, Ziemer G, Wendel H P (2008) CELL-SELEX: Novel Perspectives of Aptamer-Based Therapeutics. Int J Mol Sci 9:668-78
18. Huang Y F, Shangguan D, Liu H, Phillips J A, Zhang X, Chen Y, Tan W (2009) Molecular Assembly of an Aptamer-Drug Conjugate for Targeted Drug Delivery to Tumor Cells. Chembiochem 10:862-868
19. Kohn D B, Bauer G, Rice C R, Rothschild J C, Carbonaro D A, Valdez P, Hao Q, Zhou C, Bahner I, Kearns K, Brody K, Fox S, Haden E, Wilson K, Salata C, Dolan C, Wetter C, Aguilar-Cordova E, Church J (1999) A clinical trial of retroviral-mediated transfer of a rev-responsive element decoy gene into CD34(+) cells from the bone marrow of human immunodeficiency virus-1-infected children. Blood 94:368-71
20. McGuire M J, Li S, Brown K C (2009) Biopanning of phage displayed peptide libraries for the isolation of cell-specific ligands. Methods Mol Biol 504:291-321

21. McNamara J O, 2nd, Andrechek E R, Wang Y, Viles K D, Rempel R E, Gilboa E, Sullenger B A, Giangrande P H (2006) Cell type-specific delivery of siRNAs with aptamer-siRNA chimeras. Nat Biotechnol 24:1005-15
22. Mi J, Liu Y, Rabbani Z N, Yang Z, Urban J H, Sullenger B A, Clary B M (2010) In vivo selection of tumor-targeting RNA motifs. Nat Chem Biol 6:22-4
23. Mi Z, Guo H, Russell M B, Liu Y, Sullenger B A, Kuo P C (2009) RNA aptamer blockade of osteopontin inhibits growth and metastasis of MDA-MB231 breast cancer cells. Mol Ther 17:153-61
24. Nimjee S M, Rusconi C P, Sullenger B A (2005) Aptamers: an emerging class of therapeutics. Annu Rev Med 56:555-83
25. Osborne S E, Ellington A D (1997) Nucleic acid selection and the challenge of combinatorial chemistry. Chem Rev 97:349-370
26. Oyama T, Sykes K F, Samli K N, Minna J D, Johnston S A, Brown K C (2003) Isolation of lung tumor specific peptides from a random peptide library: generation of diagnostic and cell-targeting reagents. Cancer Lett 202: 219-30
27. Trepel M, Pasqualini R, Arap W (2008) Chapter 4 Screening Phage-Display Peptide Libraries for Vascular Targeted Peptides. Methods Enzymol 445C:83-106
28. Wu A M, Senter P D (2005) Arming antibodies: prospects and challenges for immunoconjugates. Nat Biotechnol 23:1137-46
29. Xiao Z, Shangguan D, Cao Z, Fang X, Tan W (2008) Cell-Specific Internalization Study of an Aptamer from Whole Cell Selection. Chemistry 14:1769-1775
30. Yan A C, Bell K M, Breeden M M, Ellington A D (2005) Aptamers: prospects in therapeutics and biomedicine. Front Biosci 10:1802-27
31. Zhang L, Radovic-Moreno A F, Alexis F, Gu F X, Basto P A, Bagalkot V, Jon S, Langer R S, Farokhzad O C (2007) Co-delivery of hydrophobic and hydrophilic drugs from nanoparticle-aptamer bioconjugates. ChemMedChem 2:1268-71
32. Zhou J, Li H, Li S, Zaia J, Rossi J J (2008) Novel dual inhibitory function aptamer-siRNA delivery system for HIV-1 therapy. Mol Ther 16:1481-9.

What is claimed is:

1. A process of preparing a nucleoside analog-containing-oligonucleotide for selective introduction into a subject's cells, the process comprising selecting a targeted aptamer via iterative rounds of selection against the subject's cells or against cells corresponding to the subject's cells to which the oligonucleotide is to be selectively introduced, then modifying the selected targeted aptamer with a 24 nucleotide extension, and then hybridizing a nucleoside analog-containing-oligonucleotide sufficiently complementary to hybridize to the modified selected targeted aptamer so as to prepare the nucleoside analog-containing-oligonucleotide, wherein the targeted aptamer comprises the oligonucleotide sequence set forth in SEQ ID NO: 1, 2, 3, 4, 5, 11 or 12, or wherein the modified selected targeted aptamer comprises the oligonucleotide sequence set forth in SEQ ID NO: 6.

2. The process of claim 1, wherein the nucleoside analog is a cytotoxic drug.

3. The process of claim 2, further comprising administering the nucleoside analog-containing-oligonucleotide hybridized to the targeted aptamer to a subject so as to selectively introduce the nucleoside analog into a cell.

4. The process of claim 3, wherein the nucleoside analog is cytosine arabinoside, fludarabine, cladribine, acyclovir, 2',3'-dideoxyinosine; 9-β-D-ribofuranosyladenine; 1β-arabinofuranosylcytosine; arabinosylcytosine; 4-amino-5-fluoro-1-[(2R,5 S)-2-(hydroxymethyl)-1,3-oxathiolan-5-yl]-1,2-dihydropyrimidin-2-one; 2',3'-dideoxy-3'-thiacytidine; 2'-3'-dideoxycytidine; {(1 S,4R)-4-[2-amino-6-(cyclopropylamino)-9H-purin-9-yl]cyclopent-2-en-1-yl}methanol; 2-Amino-9-[(1S,3R,4S)-4-hydroxy-3-(hydroxymethyl)-2-methylidenecyclopentyl]-6,9-dihydro-3H-purin-6-one; 2'-3'-didehydro-2'-3'-dideoxythymidine; 1-(2-deoxy-β-L-erythro-pentofuranosyl)-5-methylpyrimidine-2,4(1H,3H)-dione; 1-[(2R,4S,5S)-4-azido-5-(hydroxymethyl)oxolan-2-yl]-5-methylpyrimidine-2,4-dione; 1-[(2R,4S,5R)-4-hydroxy-5-(hydroxymethyl)oxolan-2-yl]-5-iodo-1,2,3,4-tetrahydropyrimidine-2,4-dione; 1-[4-hydroxy-5-(hydroxymethyl)oxolan-2-yl]-5-(trifluoromethyl)pyrimidine-2,4-dione; 5-Fluoro-2'-deoxycytidine; 5-Fluorodeoxycytidine; Floxuridine (5-Fluoro-1-[4-hydroxy-5-(hydroxymethyl)tetrahydrofuran-2-yl]-1H-pyrimidine-2,4-dione); 4-amino-1-(2-deoxy-2,2-difluoro-β-D-erythro-pentofuranosyl)pyrimidin-2(1H)-one; 2',2'-difluoro-2'-deoxycytidine; or (8R)-3-(2-deoxy-β-D-erythro-pentofuranosyl)-3,4,7,8-tetrahydroimidazo[4,5-d][1,3]diazepin-8-ol.

* * * * *

SEQUENCE LISTING

```
<160> NUMBER OF SEQ ID NOS: 12

<210> SEQ ID NO 1
<211> LENGTH: 120
<212> TYPE: DNA
<213> ORGANISM: ARTIFICIAL SEQUENCE
<220> FEATURE:
<223> OTHER INFORMATION: APTAMER DIRECTED TO HUMAN TRANSFERRIN CD71

<400> SEQUENCE: 1
gggaggtgaa tggttctacg attcaaacat ctcacagatc aatccaaggg acctcgttaa      60
aggacgactc ccttacatgc gagatgacca cgtaaggaat taaatgcccg ccatgaccag     120

<210> SEQ ID NO 2
<211> LENGTH: 124
<212> TYPE: DNA
<213> ORGANISM: ARTIFICIAL SEQUENCE
<220> FEATURE:
<223> OTHER INFORMATION: APTAMER DIRECTED TO HUMAN TRANSFERRIN CD71

<400> SEQUENCE: 2
gggaggtgaa tggttctacg attaggttag cggcagatca ctacaaagcc cctagagcac      60
atgctccacc gctttacatg ccgagatgac caccgtaata gaattaaatg cccgccatga     120
ccag                                                                  124

<210> SEQ ID NO 3
<211> LENGTH: 121
<212> TYPE: DNA
<213> ORGANISM: ARTIFICIAL SEQUENCE
<220> FEATURE:
<223> OTHER INFORMATION: APTAMER DIRECTED TO HUMAN TRANSFERRIN CD71

<400> SEQUENCE: 3
gggaggtgaa tggttctacg atcattacgg ctaccccgtg taacgtctag ccaaagtagt      60
accaaaagtc agttacatgc gagatgacca cgtaattgaa ttaaatgccc gccatgacca    120
g                                                                    121

<210> SEQ ID NO 4
<211> LENGTH: 43
<212> TYPE: DNA
```

```
<213> ORGANISM: ARTIFICIAL SEQUENCE
<220> FEATURE:
<223> OTHER INFORMATION: APTAMER DIRECTED TO HUMAN TRANSFERRIN CD71

<400> SEQUENCE: 4
gggggatcaa tccaagggac ccggaaacgc tcccttacac ccc                    43

<210> SEQ ID NO 5
<211> LENGTH: 44
<212> TYPE: DNA
<213> ORGANISM: ARTIFICIAL SEQUENCE
<220> FEATURE:
<223> OTHER INFORMATION: APTAMER DIRECTED TO HUMAN TRANSFERRIN CD71

<400> SEQUENCE: 5
gggggatcaa tccggctacc ccgtgtaacg tctagccaca cccc                   44

<210> SEQ ID NO 6
<211> LENGTH: 68
<212> TYPE: DNA
<213> ORGANISM: ARTIFICIAL SEQUENCE
<220> FEATURE:
<223> OTHER INFORMATION: APTAMER DIRECTED TO HUMAN TRANSFERRIN CD71

<400> SEQUENCE: 6
gggggatcaa tccggctacc ccgtgtaacg tctagccaca ccccgaatta atgcccgcc   60 atgaccag                                                           68

<210> SEQ ID NO 7
<211> LENGTH: 24
<212> TYPE: DNA
<213> ORGANISM: ARTIFICIAL SEQUENCE
<220> FEATURE:
<223> OTHER INFORMATION: APTAMER DIRECTED TO HUMAN TRANSFERRIN CD71
<220> FEATURE:
<221> NAME/KEY: misc_feature
<222> LOCATION: (1)..(1)
<223> OTHER INFORMATION: 5-fluorodeoxycytidine
<220> FEATURE:
<221> NAME/KEY: misc_feature
<222> LOCATION: (3)..(4)
<223> OTHER INFORMATION: 5-fluorodeoxycytidine
<220> FEATURE:
<221> NAME/KEY: misc_feature
<222> LOCATION: (6)..(6)
<223> OTHER INFORMATION: 5-fluorodeoxycytidine
<220> FEATURE:
<221> NAME/KEY: misc_feature
<222> LOCATION: (10)..(11)
<223> OTHER INFORMATION: 5-fluorodeoxycytidine
<220> FEATURE:
<221> NAME/KEY: misc_feature
<222> LOCATION: (13)..(13)
<223> OTHER INFORMATION: 5-fluorodeoxycytidine
<220> FEATURE:
<221> NAME/KEY: misc_feature
<222> LOCATION: (15)..(15)
<223> OTHER INFORMATION: 5-fluorodeoxycytidine
<220> FEATURE:
<221> NAME/KEY: misc_feature
<222> LOCATION: (18)..(18)
<223> OTHER INFORMATION: 5-fluorodeoxycytidine
<220> FEATURE:
<221> NAME/KEY: misc_feature
<222> LOCATION: (20)..(20)
<223> OTHER INFORMATION: 5-fluorodeoxycytidine

<400> SEQUENCE: 7
ctcctcatgc cgcgcatctc atta                                         24
```

```
<210> SEQ ID NO 8
<211> LENGTH: 41
<212> TYPE: DNA
<213> ORGANISM: ARTIFICIAL SEQUENCE
<220> FEATURE:
<223> OTHER INFORMATION: APTAMER DIRECTED TO HUMAN PROTEIN KINASE 7

<400> SEQUENCE: 8
atctaactgc tgcgccgccg ggaaaatact gtacggttag a                           41

<210> SEQ ID NO 9
<211> LENGTH: 41
<212> TYPE: DNA
<213> ORGANISM: ARTIFICIAL SEQUENCE
<220> FEATURE:
<223> OTHER INFORMATION: APTAMER DIRECTED TO PROTEIN KINASE 7
<220> FEATURE:
<221> NAME/KEY: modified_base
<222> LOCATION: (2)..(2)
<223> OTHER INFORMATION: 5FdU
<220> FEATURE:
<221> NAME/KEY: modified_base
<222> LOCATION: (4)..(4)
<223> OTHER INFORMATION: 5FdU
<220> FEATURE:
<221> NAME/KEY: modified_base
<222> LOCATION: (8)..(8)
<223> OTHER INFORMATION: 5FdU
<220> FEATURE:
<221> NAME/KEY: modified_base
<222> LOCATION: (37)..(38)
<223> OTHER INFORMATION: 5FdU

<400> SEQUENCE: 9
aucuaacugc tgcgccgccg ggaaaatact gtacgguuag a                           41

<210> SEQ ID NO 10
<211> LENGTH: 41
<212> TYPE: RNA
<213> ORGANISM: ARTIFICIAL SEQUENCE
<220> FEATURE:
<223> OTHER INFORMATION: APTAMER DIRECTED TO HUMAN PROTEIN KINASE 7
<220> FEATURE:
<221> NAME/KEY: modified_base
<222> LOCATION: (2)..(2)
<223> OTHER INFORMATION: 5FdU
<220> FEATURE:
<221> NAME/KEY: modified_base
<222> LOCATION: (4)..(4)
<223> OTHER INFORMATION: 5FdU
<220> FEATURE:
<221> NAME/KEY: modified_base
<222> LOCATION: (8)..(8)
<223> OTHER INFORMATION: 5FdU
<220> FEATURE:
<221> NAME/KEY: modified_base
<222> LOCATION: (11)..(11)
<223> OTHER INFORMATION: 5FdU
<220> FEATURE:
<221> NAME/KEY: modified_base
<222> LOCATION: (27)..(27)
<223> OTHER INFORMATION: 5FdU
<220> FEATURE:
<221> NAME/KEY: modified_base
<222> LOCATION: (30)..(30)
<223> OTHER INFORMATION: 5FdU
<220> FEATURE:
<221> NAME/KEY: modified_base
<222> LOCATION: (32)..(32)
<223> OTHER INFORMATION: 5FdU
<220> FEATURE:
<221> NAME/KEY: modified_base
<222> LOCATION: (37)..(38)
<223> OTHER INFORMATION: 5FdU
```

```
<400> SEQUENCE: 10
aucuaacugc ugcgccgccg ggaaaauacu guacgguuag a                    41

<210> SEQ ID NO 11
<211> LENGTH: 121
<212> TYPE: RNA
<213> ORGANISM: ARTIFICIAL SEQUENCE
<220> FEATURE:
<223> OTHER INFORMATION: APTAMER DIRECTED AT MOUSE CELL LINE

<400> SEQUENCE: 11
gggaggugaa ugguucuacg auauugcgaa uccucuaucc guucuaaacg cuuuaugauu    60
ucgcauaguc cuuacaugcg agaugaccac cguaauugaa uuaaaugccc gccaugacca   120
g                                                                  121

<210> SEQ ID NO 12
<211> LENGTH: 41
<212> TYPE: RNA
<213> ORGANISM: ARTIFICIAL SEQUENCE
<220> FEATURE:
<223> OTHER INFORMATION: APTAMER DIRECTED AT MOUSE CELL LINE

<400> SEQUENCE: 12
ugcgaauccu cuauccguuc uaaacgcuuu augauucgc a                     41
```